United States Patent
Bieberich et al.

(10) Patent No.: US 8,226,294 B2
(45) Date of Patent: Jul. 24, 2012

(54) FLEXIBLE DEEP TISSUE TEMPERATURE MEASUREMENT DEVICES

(75) Inventors: Mark T. Bieberich, Edina, MN (US);
Clifford T. Jue, Santa Cruz, CA (US);
Jonathan I. Kaplan, Palo Alto, CA (US); Brian J. Mason, Menlo Park, CA (US); Paul J. Silberschatz, San Francisco, CA (US); Albert P. Van Duren, Chaska, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 568 days.

(21) Appl. No.: 12/584,108

(22) Filed: Aug. 31, 2009

(65) Prior Publication Data
US 2011/0051776 A1 Mar. 3, 2011

(51) Int. Cl.
*G01K 7/00* (2006.01)
(52) U.S. Cl. .......... 374/163; 374/183; 374/208
(58) Field of Classification Search .......... 374/163, 374/164, 166, 208, E07.001, E15.001
See application file for complete search history.

(56) References Cited

U.S. PATENT DOCUMENTS

| | | |
|---|---|---|
| 1,363,259 A | 12/1920 | Mills |
| 1,526,641 A | 2/1925 | Mulvany et al. |
| 1,528,383 A | 3/1925 | Schmidt |
| 1,638,943 A | 8/1927 | Little |
| 2,378,804 A | 6/1945 | Sparrow et al. |
| 2,381,819 A | 8/1945 | Graves et al. |
| 2,519,785 A | 8/1950 | Okolicsanyi |
| 2,629,757 A | 2/1953 | McKay |
| 2,807,657 A | 9/1957 | Jenkins et al. .......... 136/4 |
| 2,969,141 A | 1/1961 | Katzin .......... 206/16.5 |
| 3,099,575 A | 7/1963 | Hill .......... 117/212 |
| 3,099,923 A | 8/1963 | Benzinger .......... 73/341 |
| 3,215,265 A | 11/1965 | Welin-Berger .......... 206/63.2 |
| 3,235,063 A | 2/1966 | Jarund .......... 206/16.5 |
| 3,238,775 A | 3/1966 | Watts .......... 73/190 |
| 3,301,394 A | 1/1967 | Baermann et al. .......... 206/63.2 |

(Continued)

FOREIGN PATENT DOCUMENTS
CA 2 538 940 A1 6/2006
(Continued)

OTHER PUBLICATIONS
Togawa, T, et al, A modified internal temperature measurement device, *Medical and Biological Engineering*, May 1976, pp. 361-364.

(Continued)

*Primary Examiner* — Yaritza Guadalupe-McCall
(74) *Attorney, Agent, or Firm* — Adam Bramwell; Terrance A. Meador

(57) ABSTRACT

The invention pertains to flexible devices used for zero-heat-flux, deep tissue temperature measurement, especially to disposable temperature measurement devices. Such a device is constituted of a flexible substrate with a plurality of contiguous sections. An electrical circuit is disposed on a side of the substrate. The electrical circuit includes first and second thermal sensors disposed, respectively, on first and second substrate sections. A heater trace is disposed on the first substrate section with the first thermal sensor. The first and second sections are folded together to position the first and second thermal sensors therebetween, and a flexible insulator disposed between the folded-together first and second sections maintains the first and second thermal sensors in a spaced-apart relationship.

26 Claims, 6 Drawing Sheets

U.S. PATENT DOCUMENTS

| | | | | |
|---|---|---|---|---|
| 3,367,182 | A | 2/1968 | Baxter | 73/190 |
| 3,427,209 | A | 2/1969 | Hager, Jr. | 136/225 |
| 3,469,685 | A | 9/1969 | Baermann | 206/63.2 |
| 3,552,558 | A | 1/1971 | Poncy | 206/63.2 |
| 3,581,570 | A | 6/1971 | Wortz | 73/355 R |
| 3,607,445 | A | 9/1971 | Hines | 136/225 |
| 3,720,103 | A | 3/1973 | Adams et al. | 73/190 H |
| 3,767,470 | A | 10/1973 | Hines | 136/225 |
| 3,781,749 | A | 12/1973 | Iles et al. | 338/25 |
| 3,809,230 | A | 5/1974 | Poncy | 206/306 |
| 3,833,115 | A | 9/1974 | Schapker | 206/63.2 |
| 3,877,463 | A | 4/1975 | Cary et al. | 128/2 H |
| 3,933,045 | A | 1/1976 | Fox et al. | 73/359 |
| 3,942,123 | A | 3/1976 | Georgi | 328/1 |
| 4,022,063 | A | 5/1977 | West et al. | 73/362 |
| 4,024,312 | A | 5/1977 | Korpman | 428/343 |
| 4,142,631 | A | 3/1979 | Brandriff | 206/306 |
| 4,253,469 | A | 3/1981 | Aslan | 128/736 |
| 4,275,741 | A | 6/1981 | Edrich | 128/653 |
| 4,347,854 | A | 9/1982 | Gosline et al. | 128/736 |
| 4,407,292 | A | 10/1983 | Edrich | 128/653 |
| 4,494,550 | A | 1/1985 | Blazek et al. | 128/664 |
| 4,539,994 | A | 9/1985 | Baumbach et al. | 128/635 |
| 4,541,734 | A | 9/1985 | Ishizaka | 374/169 |
| 4,572,213 | A | 2/1986 | Kawahara | 128/736 |
| 4,574,359 | A | 3/1986 | Ishizaka et al. | 364/557 |
| 4,577,976 | A | 3/1986 | Hayashi et al. | 374/29 |
| 4,592,000 | A | 5/1986 | Ishizaka et al. | 364/557 |
| 4,629,336 | A | 12/1986 | Ishizaka | 364/557 |
| 4,648,055 | A | 3/1987 | Ishizaka et al. | 364/557 |
| 4,652,145 | A | 3/1987 | Bjornberg | 374/194 |
| 4,669,049 | A | 5/1987 | Kosednar et al. | 364/557 |
| 4,747,413 | A | 5/1988 | Bloch | 128/736 |
| 4,841,543 | A | 6/1989 | Dittmar et al. | 374/44 |
| 4,859,078 | A | 8/1989 | Bowman et al. | 374/44 |
| 4,899,297 | A | 2/1990 | Sano et al. | 364/557 |
| 4,955,380 | A | 9/1990 | Edell | 128/635 |
| 4,987,579 | A | 1/1991 | Yoshinaka et al. | 377/25 |
| 5,002,057 | A | 3/1991 | Brady | 128/652 |
| 5,015,102 | A | 5/1991 | Yamaguchi | 374/169 |
| 5,033,866 | A | 7/1991 | Kehl et al. | 374/179 |
| 5,040,901 | A | 8/1991 | Suzuki | 374/183 |
| 5,050,612 | A | 9/1991 | Matsumura | 128/670 |
| 5,062,432 | A | 11/1991 | James et al. | 128/736 |
| 5,088,837 | A | 2/1992 | Shiokawa et al. | 374/185 |
| 5,149,200 | A | 9/1992 | Shiokawa et al. | 374/185 |
| 5,172,979 | A | 12/1992 | Barkley et al. | 374/147 |
| 5,178,468 | A | 1/1993 | Shiokawa et al. | 374/185 |
| 5,199,436 | A | 4/1993 | Pompei et al. | 128/664 |
| 5,255,979 | A | 10/1993 | Ferrari | 374/158 |
| 5,263,775 | A | 11/1993 | Smith et al. | 374/134 |
| 5,293,877 | A | 3/1994 | O'Hara et al. | 128/736 |
| 5,483,190 | A | 1/1996 | McGivern | 327/34 |
| 5,516,581 | A | 5/1996 | Kreckel et al. | 428/317.3 |
| 5,576,224 | A * | 11/1996 | Yakura et al. | 374/184 |
| 5,816,706 | A | 10/1998 | Heikkila et al. | 374/134 |
| 5,884,235 | A | 3/1999 | Ebert | 702/87 |
| 5,990,412 | A | 11/1999 | Terrell | 136/225 |
| 5,993,698 | A | 11/1999 | Frentzel et al. | 252/511 |
| 6,001,471 | A | 12/1999 | Bries et al. | 428/343 |
| 6,014,890 | A | 1/2000 | Breen | 73/29.02 |
| 6,019,507 | A | 2/2000 | Takaki | 374/161 |
| 6,059,452 | A | 5/2000 | Smith et al. | 374/185 |
| 6,203,191 | B1 | 3/2001 | Mongan | 374/43 |
| 6,220,750 | B1 | 4/2001 | Palti | 374/164 |
| 6,224,543 | B1 | 5/2001 | Gammons et al. | 600/124 |
| 6,231,962 | B1 | 5/2001 | Bries et al. | 428/317.3 |
| 6,253,098 | B1 | 6/2001 | Walker et al. | 600/344 |
| 6,255,622 | B1 | 7/2001 | May et al. | 219/209 |
| 6,278,051 | B1 | 8/2001 | Peabody | 136/225 |
| 6,280,397 | B1 | 8/2001 | Yarden et al. | 600/549 |
| 6,283,632 | B1 | 9/2001 | Takaki | 374/161 |
| 6,292,685 | B1 | 9/2001 | Pompei | 600/474 |
| 6,312,391 | B1 | 11/2001 | Ramadhyani et al. | 600/549 |
| 6,355,916 | B1 | 3/2002 | Siefert | 219/494 |
| 6,377,848 | B1 | 4/2002 | Garde et al. | 604/20 |
| 6,398,727 | B1 | 6/2002 | Bui et al. | 600/300 |
| 6,495,806 | B2 | 12/2002 | Siefert | 219/494 |
| 6,553,243 | B2 | 4/2003 | Gurley | 600/340 |
| 6,595,929 | B2 | 7/2003 | Stivoric et al. | 600/549 |
| 6,676,287 | B1 | 1/2004 | Mathis et al. | 374/1 |
| 6,773,405 | B2 | 8/2004 | Fraden et al. | 600/549 |
| 6,827,487 | B2 | 12/2004 | Baumbach | 374/164 |
| 6,886,978 | B2 | 5/2005 | Tokita et al. | 374/169 |
| 6,929,611 | B2 | 8/2005 | Koch | 600/549 |
| 7,059,767 | B2 | 6/2006 | Tokita et al. | 374/163 |
| 7,270,476 | B2 | 9/2007 | Tokita et al. | 374/107 |
| 7,299,090 | B2 | 11/2007 | Koch | 600/547 |
| 7,306,283 | B2 | 12/2007 | Howick et al. | 297/180.12 |
| 7,318,004 | B2 | 1/2008 | Butterfield | 702/130 |
| 7,354,195 | B2 | 4/2008 | Sakano | 374/208 |
| 7,364,356 | B2 | 4/2008 | Dicks et al. | 374/121 |
| 7,410,291 | B2 | 8/2008 | Koch | 374/163 |
| 7,426,872 | B2 | 9/2008 | Dittmar et al. | 73/818 |
| 8,089,245 | B2 * | 1/2012 | Kato et al. | 320/108 |
| 2002/0097775 | A1 | 7/2002 | Hamouda et al. | 374/29 |
| 2003/0130590 | A1 | 7/2003 | Bui et al. | 600/537 |
| 2004/0210280 | A1 | 10/2004 | Liedtke | 607/96 |
| 2005/0245839 | A1 | 11/2005 | Stivoric et al. | 600/549 |
| 2005/0281314 | A1 * | 12/2005 | Fraden | 374/163 |
| 2007/0167859 | A1 | 7/2007 | Finneran et al. | 600/546 |
| 2007/0206655 | A1 | 9/2007 | Haslett et al. | 374/141 |
| 2007/0282218 | A1 | 12/2007 | Yarden | 600/549 |
| 2008/0170600 | A1 | 7/2008 | Sattler et al. | 374/163 |
| 2010/0134122 | A1 * | 6/2010 | Furumura et al. | 374/183 |
| 2010/0220766 | A1 * | 9/2010 | Burgard | 374/183 |
| 2010/0268113 | A1 * | 10/2010 | Bieberich | 600/549 |
| 2011/0051776 | A1 * | 3/2011 | Bieberich et al. | 374/163 |
| 2011/0249699 | A1 * | 10/2011 | Bieberich et al. | 374/1 |
| 2011/0249701 | A1 * | 10/2011 | Bieberich et al. | 374/163 |

FOREIGN PATENT DOCUMENTS

| | | | |
|---|---|---|---|
| CA | 2 583 034 | A1 | 9/2007 |
| DE | 3527942 | A1 | 2/1987 |
| EP | 0239824 | B1 | 5/1992 |
| GB | 2266771 | A | 11/1993 |
| JP | 55-29794 | | 3/1980 |
| JP | 55029794 | | 3/1980 |
| JP | 57-183832 | | 12/1982 |
| JP | 2002202205 | A | 7/2002 |
| JP | 2007212407 | A | 8/2007 |
| JP | 2009080000 | A | 4/2009 |
| WO | 99/60356 | A1 | 11/1999 |
| WO | 00/58702 | A1 | 10/2000 |
| WO | 01/31305 | A1 | 5/2001 |
| WO | 02/066946 | A2 | 8/2002 |
| WO | 2007/060609 | A2 | 5/2007 |
| WO | 2008/068665 | A1 | 6/2008 |
| WO | 2008/078271 | A1 | 7/2008 |
| WO | 2009/141780 | A1 | 11/2009 |
| WO | 2010/082102 | A2 | 7/2010 |
| WO | 2010/103436 | A1 | 9/2010 |
| WO | 2010/116297 | A1 | 10/2010 |
| WO | 2010/120360 | A1 | 10/2010 |
| WO | 2010/120362 | A1 | 10/2010 |
| WO | WO 2011/025521 | A1 | 10/2010 |
| WO | WO 2011/126543 | A1 | 10/2011 |
| WO | WO 2011/146098 | A1 | 11/2011 |

OTHER PUBLICATIONS

Zhang X, et al, Application of the Heat Flux Meter in Physiological Studies, *J. therm. Biol.*, 1993, vol. 18: 473-476.Yamakage M, et al, Deep temperature monitoring—comparative study between conventional and new developed monitors, *Anesthesiology*, 2002; 96: A501.

Suleman M-I, et al, Insufficiency in a new temporal-artery thermometer for adult and pediatric patients, *Anesth Analg*, 2002; 95: 67-71.

Yamakage M, Evaluation of a newly developed monitor of deep body temperature, *J. Anesth.*, 2002; 16:354-357.

Thurbide, K., Excuse me, but my Band-Aid is beeping, Haslett's smart Band-Aid/University of Calgary, Jul. 18, 2007, pp. 1-2.

Langham Ge, et al, Noninvasive temperature monitoring in postanesthesia care units, *Anesthesiology*, 2009, 111; 1:1-7.

Kitamura, K, et al, Development of a new method for the noninvasive measurement of deep body temperature without a heater, *Med. Eng. Phys.*, 2010; 32(1): 1-6. Epub Nov. 10, 2009.

Zeiner A, et al, Non-invasive continuous cerebral temperature monitoring in patients treated with mild therapeutic hypothermia: an observational pilot study, *Resuscitation*, Jul. 2010; 81(7) 861-866. Epub Apr. 15, 2010.

International Search Report and Written Opinion, PCT/US2010/001108, mailed Jul. 23, 2010.

International Search Report and Written Opinion, PCT/US2010/001104, mailed Jul. 26, 2010.

International Search Report and Written Opinion, PCT/US2010/002185, mailed Dec. 13, 2010.

Fox RH, et al, A new technique for monitoring the deep body temperature in man from the intact skin surface. *J. Physiol.* 1971; 212(2): 8P-10P.

Solman AJ, et al, New thermometers for deep tissue temperature. *Biomedical Engineering* 1973; 8(10): 432-435.

Fox RH, et al, A new method for monitoring deep body temperature from the skin surface. *Clin. Sci.* 1973; 44: 81-86.

Togawa T, Non-invasive deep body temperature measurement. In: Rolfe P (ed) *Non-invasive Physiological Measurements.* 1979; vol. 1: 261-277.

Gunga H-C, et al, A non-invasive device to continuously determine heat strain in humans. *J. Ther. Bio.* 2008; 33: 297-307.

Kimberger O, Accuracy and precision of a novel non-invasive core thermometer. *BJA.* 2009; 103(2): 226-231.

International Search Report and Written Opinion, PCT/US2011/000549, mailed Jun. 26, 2011.

International Search Report and Written Opinion, PCT/US2011/000552, mailed Jun. 29, 2011.

* cited by examiner

FLEXIBLE DEEP TISSUE TEMPERATURE MEASUREMENT DEVICES

BACKGROUND

The subject matter relates to a device for use in the estimation of deep tissue temperature (DTT), a temperature of human or animal tissue at some distance beneath the skin. For example, the core temperature of a human body can be measured indirectly using a disposable temperature device placed on surface tissue (such as skin). The temperature of the surface tissue is read as the core temperature.

Noninvasive measurement of deep tissue temperature by means of a zero-heat-flux device was described by Fox and Solman in 1971 (Fox R H, Solman A J. A new technique for monitoring the deep body temperature in man from the intact skin surface. J. Physiol. January 1971:212(2): pp 8-10). The Fox/Solman system, illustrated in FIG. 1, estimates body core temperature by indirect means using a specially designed measurement device 10 that stops or blocks heat flow through a portion of the skin. The components of the device 10 are contained in a housing 11. The device 10 includes two thermistors 20 mounted on either side of a thermal resistance 22. The thermal resistance 22 maintains the thermistors in a spaced-apart arrangement in which the thermistors are positioned on separate sides of the thermal resistance, along a line that is generally perpendicular to a region of skin on a person's body where deep tissue temperature is to be measured. A heater 24 is disposed at the top of the device 10, over the elements 20, 22, and 24. In use, the device 10 is placed on the region of skin. With the bottom surface 26 of the device resting on the person's body, in contact with the region, the thermistors 20 measure a temperature difference, or error signal, across the thermal resistance 22. The error signal is used to drive a heater controller 30 comprising a transistor switch and a control circuit for opening and closing the switch. The controller 30 operates to minimize the error signal by causing the heater 24 to provide just enough heat to equalize the temperature on both sides of the thermal resistance 22. When the temperatures sensed by the thermistors 20 are equal, there is no heat flow through the device, and the temperature measured by the lower thermistor 20 by way of a temperature meter circuit constituted of an amplifier 36 and a temperature meter 38 is equivalent to DTT. The device 10 essentially acts as a thermal insulator that blocks heat flow through the thermal resistor 22; DTT measurement devices that operate in the same manner are termed "zero heat flux" ("ZHF") devices. Since the heater 24 operates to guard against loss of heat along the path of measurement through the device, it is often referred to as a "guard heater".

Togawa improved the Fox/Solman system with a DTT measurement device structure that accounted for the strong influence of dermal blood flow on heat transfer through the skin. (Togawa T. Non-Invasive Deep Body Temperature Measurement. In: Rolfe P (ed) Non-Invasive Physiological Measurements. Vol. 1. 1979. Academic Press, London, pp. 261-277). The device, illustrated in FIG. 2, encloses Fox and Solman's ZHF design, which blocks heat flow normal to the body, in a thick aluminum housing with a cylindrical annulus construction that also reduces or eliminates radial heat flow from the center to the periphery of the device.

Fox/Solman and Togawa have shown that heat flux normal to the body is useful to control the operation of a heater that blocks heat flow through a thermal resistance. This results in a construction that stacks components, which gives the DTT measurement device a substantial vertical profile. The thermal mass added by Togawa's cover improves the stability of the Fox/Solman design. Basic engineering for heat flux measurement would suggest that a large thermal resistance in the device makes the measurement more accurate, but it will also slow the transient response rate. Since the goal is zero heat flux across the device, the more thermal resistance the better. However, additional thermal resistance adds mass and size, and also increases the time required to reach a stable temperature.

Measurement of body core temperature is desirable for many reasons. For example, maintenance of core temperature in a normothermic range during a perioperative cycle has been shown to reduce the incidence of surgical site infection; and so it is beneficial to monitor a patient's body core temperature before, during, and after surgery. Of course noninvasive measurement is very desirable, for the comfort and the safety of a patient. Deep tissue temperature measurement using a measurement device supported on the skin provides an accurate and noninvasive means for monitoring body core temperature. However, the size and mass and cost of the Fox/Solman and Togawa devices do not promote disposability. Consequently, they must be sanitized after each use, and stored for reuse. As a result, use of these devices to measure deep tissue temperature may raise the costs associated with DTT measurement and may increase the risk of cross contamination between patients. It is therefore useful to reduce the size and mass of a DTT measurement device, without sacrificing its performance, in order to promote disposability.

SUMMARY

An object of an invention completed in respect of the problems described above is to provide a disposable device with which deep tissue temperature can be measured noninvasively, easily, and with minimal labor, length of time, and cost.

The object is achieved with a disposable temperature measurement device constituted of a flexible substrate and an electrical circuit disposed on a surface of the flexible substrate. The electrical circuit includes a heater trace having a pattern surrounding a zone of the surface, a first thermal sensor disposed in the zone, a second thermal sensor disposed outside of the heater trace, a plurality of electrical pads disposed outside of the heater trace, and a plurality of conductive traces connecting the first and second thermal sensors and the heater trace with the plurality of electrical pads. Sections of the flexible substrate are folded together to place the first and second thermal sensors in proximity.

The temperature measurement device preferably includes a layer of flexible insulation disposed between the folded-together sections and separating the first and second thermal sensors In a preferred embodiment, a pattern of slits in the flexible substrate defines a plurality of heater zones occupied by the heater trace. Preferably, each heater zone is flexible independently of any other heater zone.

The object is also achieved with a disposable temperature measurement device constituted of a flexible substrate having first and second sides. The flexible substrate includes a circular center section and a tab and a tail extending from the center section in respective radial directions. A first thermal sensor is disposed on a first substrate side, substantially at the center of the center section, and a heater trace is disposed on the first substrate side, in the center section, around the first thermal sensor. A second thermal sensor is disposed on the first side, in the tail. The center section and the tail are folded together to place the first and second thermal sensors in proximity to each other, and a layer of flexible insulation disposed between the folded-together center section and tail maintains the first and second thermal sensors in a spaced-apart relationship.

A plurality of electrical pads is disposed on the first substrate side, in the tab, and a plurality of traces is disposed on the first side to connect the first and second thermal sensors and the heater trace with the plurality of electrical pads.

The object is also achieved with a method of temperature device manufacture that includes fabricating an electrical circuit on a first side of a flexible substrate with a center section, a tab extending from the center section, and a tail extending from the center section. The electrical circuit includes a first thermal sensor disposed on the first side, in the center section, a heater trace disposed on the first side, in the center section, around the first thermal sensor, a second thermal sensor disposed on the first side, in the tail, a plurality of electrical pads disposed on the first side, in the tab, and a plurality of traces disposed on the first side and connecting the first and second thermal sensors and the heater trace with the plurality of electrical pads. A flexible heater insulating layer is attached to the second side, over the center section, and a flexible central insulating layer is attached to the first side, over the center section. The tail is folded over the central insulating layer such that the first and second thermal sensors are maintained in a spaced relationship by the central insulating layer. A release liner is attached to the central insulating layer, over at least the central insulating layer.

DETAILED DESCRIPTION OF THE PREFERRED EMBODIMENTS

It is desirable that zero heat flux, deep tissue temperature measurement device constructions be disposable. Thus the constructions should be easy and inexpensive to fabricate and assemble, have a low mass and a low profile, and comprise inexpensive materials and parts. It is particularly desirable that disposable DTT measurement device constructions be assembled from low-profile, light weight, flexible assemblies that enable zero heat flux temperature measurement at various locations on a human or animal body.

A temperature device for zero heat flux deep tissue temperature measurement includes a flexible substrate with at least two thermal sensors disposed in a spaced-apart relationship and separated by one or more flexible layers of thermally insulating material. Preferably the sensors are maintained in a spaced apart relationship by a flexible thermal (and electrical) insulator. The substrate supports at least the thermal sensors, the separating thermal insulator, and a heater.

Although temperature device constructions are described in terms of preferred embodiments comprising representative elements, the embodiments are merely illustrative. It is possible that other embodiments will include more elements, or fewer, than described. It is also possible that some of the described elements will be deleted, and/or other elements that are not described will be added. Further, elements may be combined with other elements, and/or partitioned into additional elements.

Figure 1:
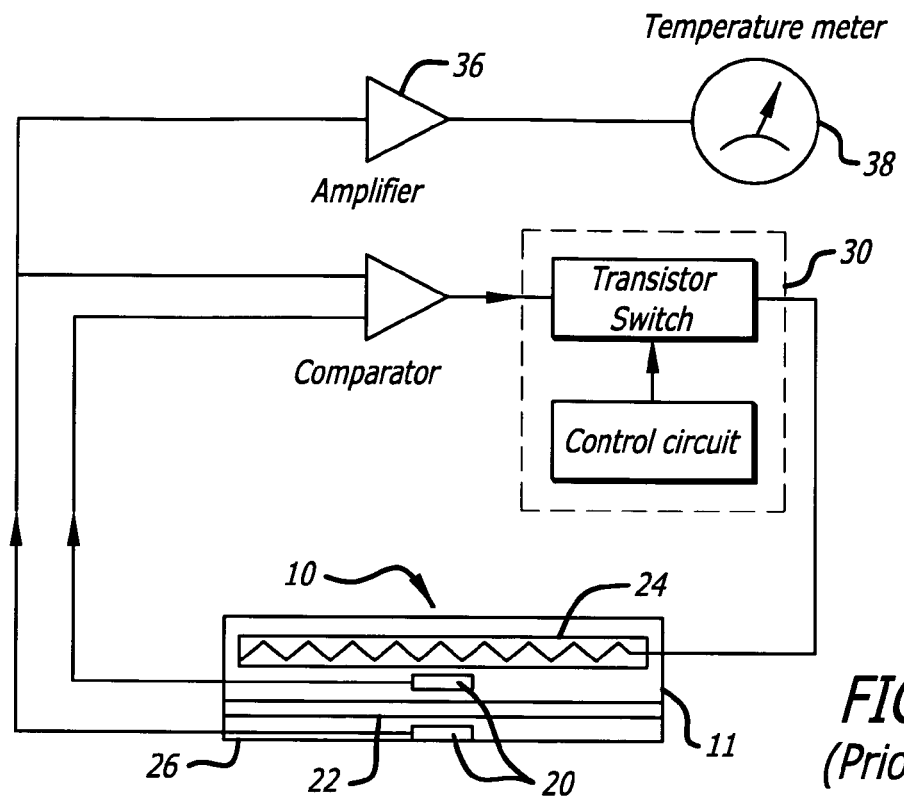
FIG. 1 is a schematic block diagram of a first prior art deep tissue temperature measurement system including a ZHF deep tissue temperature measurement device.
Figure 2:
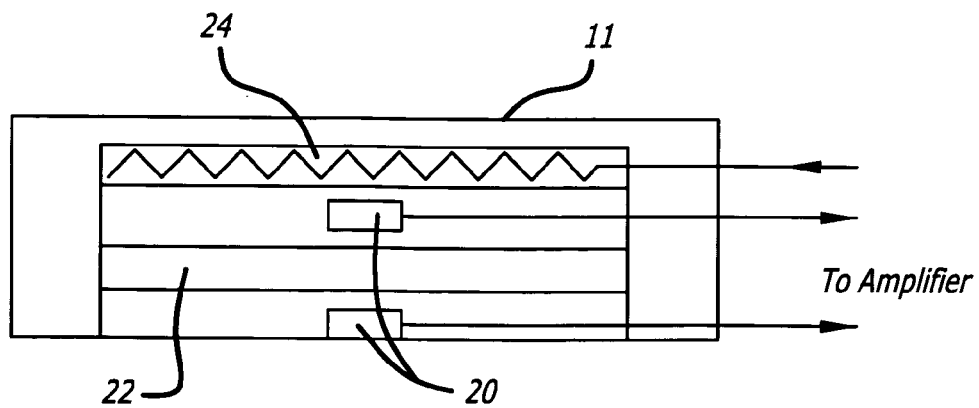
FIG. 2 is a schematic side sectional diagram of a second prior art deep tissue temperature measurement system including a ZHF deep tissue temperature measurement device with an aluminum cap.
Figure 3:
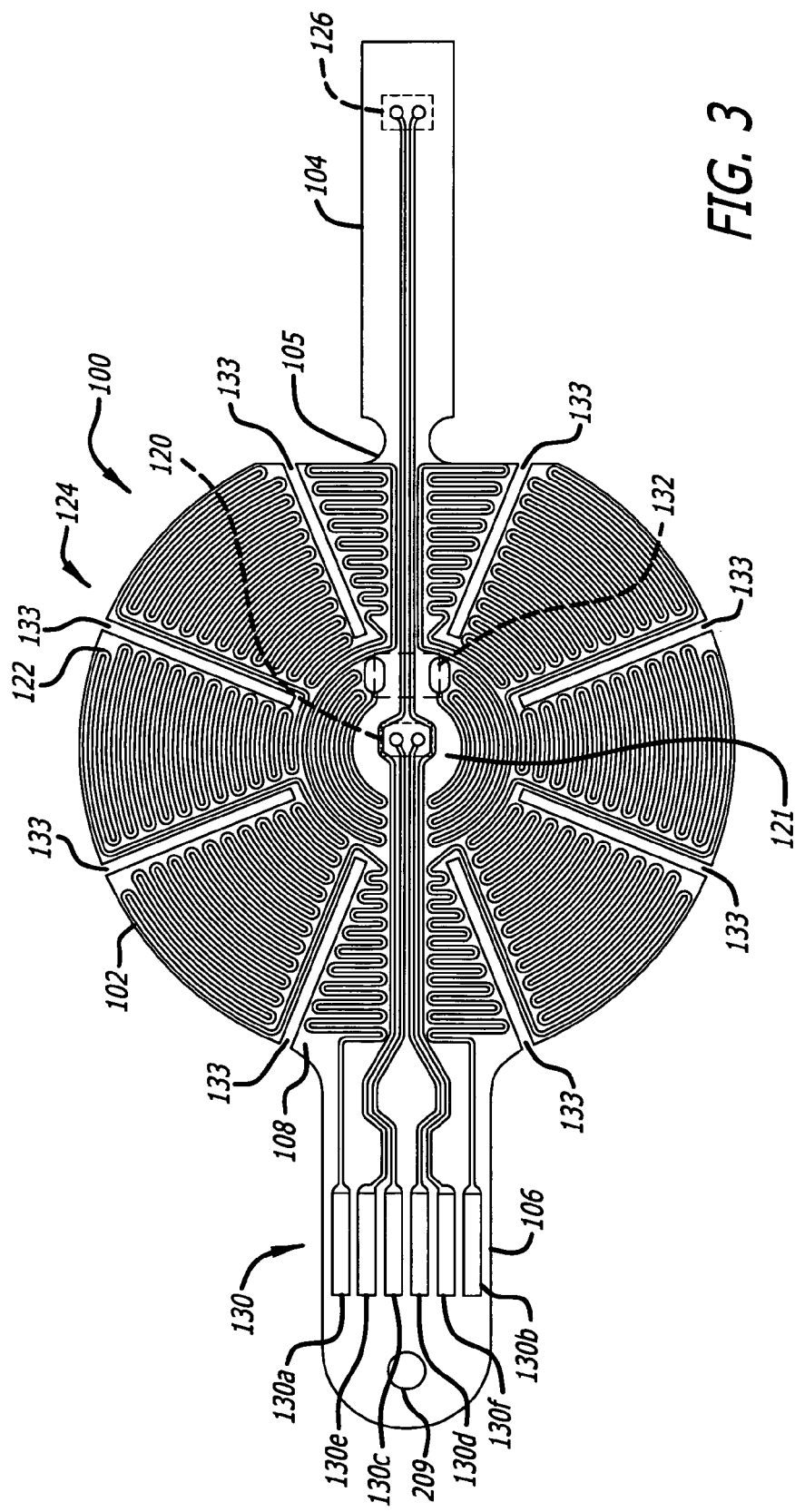
FIG. 3 is a plan view of a side of a flexible substrate showing an electrical circuit disposed on a surface of the substrate for temperature measurement.

A layout of an electrical circuit for a temperature measurement device is illustrated in FIG. 3. The electrical circuit is disposed on a flexible substrate in order to adapt or conform the physical configuration of the temperature measurement device to differing contours encountered at different temperature measurement locations. Preferably, but not necessarily, the flexible substrate is constructed or fabricated to have a plurality of contiguous sections. For example, the flexible substrate 100 has three contiguous sections 102, 104, and 106. The first, or center, section 102 is substantially circular in shape. The second section (or "tail") 104 has the shape of a narrow, elongate rectangle that extends in a first radial direction from the periphery of the first section 102. Where the center section and the tail join at 105, the periphery of the center section has a straight portion and the width of the tail is reduced. The third, or tab, section 106 has the shape of a broad, elongate rectangle that extends in a second radial direction from the periphery of the center section 102. Preferably, the tail and tab are aligned along a diameter of the center section.

As per FIG. 3, the elements of the electronic circuit are disposed on a single surface, on a first side 108 of the flexible substrate. A first thermal sensor 120 is positioned inside the outer perimeter of the center section 102, preferably, near or at the center of the center section 102. An electrically conductive heater trace 122 defines a heater with a shape that surrounds or encircles a zone 121 in which the first thermal sensor 120 is located. In the preferred embodiment illustrated in FIG. 3, the heater trace has an annular shape that includes a circular array of wedge-shaped heater zones 124 that surround or encircle the zone 121 and the first thermal sensor 120 which is disposed in the zone. A second thermal sensor 126 is positioned on the tail 104. A plurality of electrical connection pads 130 is located in the tab 106. The heater trace includes two electrically conductive trace sections that terminate in the connection pads 130a and 130b. Two electrically conductive traces extend between mounting pads on which the first thermal sensor 120 is mounted and the connection pads 130c and 130d. Two additional electrically conductive traces extend between mounting pads on which the second thermal sensor 126 is mounted and the connection pads 130e and 130f.

In the specific layout shown of the preferred embodiment shown in FIG. 3, the path of the heater trace 122 crosses the paths of the two traces for the second thermal sensor 126. In this case, the continuity of the heater trace is preferably, but not necessarily, maintained by an electrically conductive zero-ohm jumper 132 which crosses, and is electrically isolated from, the two traces for the second thermal sensor 126. In other embodiments, the continuity of the heater trace 122 can also be maintained by vias to the second side of the flexible substrate, by running the thermal sensor traces around the periphery of the first side of the flexible substrate, by a jumper wire instead of the zero-ohm resistor, or by any equivalent solution.

The flexibility or conformability of the flexible substrate can be enhanced by a plurality of slits 133 that define zones which move or flex independently of each other. In the preferred embodiment, the slits 133 are made in the center section 102 in a pattern that follows or accommodates the layout of the heater trace 122. The pattern at least partially separates the heater zones 124 so as to allow any one of the heater zones 124 to move independently of any other heater zone. The preferred pattern of slits is a radial pattern in that each slit is made along a respective radius of the circular center section 102, between adjacent heater zones, and extends along the radius from the periphery of the center section 102 toward the center of the circular shape of the section. This is not meant to exclude other possible slit configurations determined by the different shapes of the heater trace layout and the flexible substrate sections.

Sections of the flexible substrate are brought or folded together about an insulator to provide thermal resistance between the first and second thermal sensors 120 and 126 in a configuration that is preferred for ZHF temperature measurement. For example, at least the center and tail sections 102 and 104 of the flexible substrate are brought or folded together about a flexible insulator. Preferably, the first and second thermal sensors 120 and 126 are thereby disposed on respective sides of a thermal insulator. In this regard, with reference to FIGS. 3 and 4, the center section 102 and tail 104 are folded together about a flexible layer of insulating material 140. The layer 140 provides thermal and electrical resistance between the thermal sensors; it also supports the thermal sensors in a spaced-apart configuration.

Figure 4:
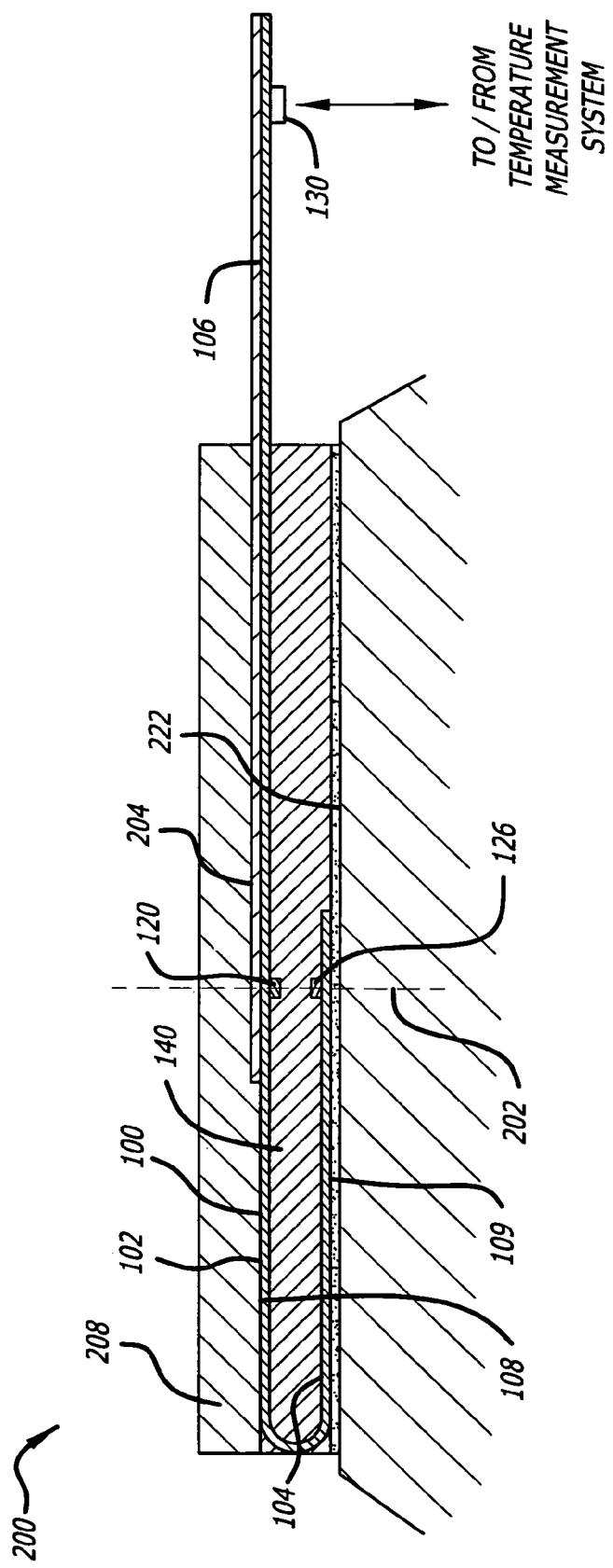
FIG. 4 is a side sectional view of a temperature device that incorporates the electrical circuit of FIG. 3.

A flexible temperature measurement device construction includes an electrical circuit laid out on a side of a flexible substrate as shown in FIG. 3. With two sections of the flexible substrate brought or folded together so as to sandwich a flexible insulator, the construction has a multilayer structure as best seen in FIG. 4. Thus, a temperature measurement device 200 includes the electrical circuit laid out on the surface of the first side 108 of the flexible substrate 100. The central and tail sections 102 and 104 are brought or folded together about the flexible insulating layer 140 so as to provide a thermal resistance between the first and second thermal sensors 120 and 126. The flexible insulating layer also maintains the first and second thermal sensors disposed in a spaced relationship. Preferably, but not necessarily, the second thermal sensor 126 is aligned with the first thermal sensor a line 202 which passes through the zone 121 that is surrounded by the heater trace (seen in FIG. 3). The temperature measurement device further includes a flexible heater insulator 208 attached to a second side 109 of the substrate 100, over the center section 102.

The layout of the electrical circuit illustrated in FIG. 3 locates all of the circuit components on a single surface on one side of the flexible substrate 100. This layout confers several advantages. First, it requires only a single fabrication sequence to lay down traces for the heater, the thermal sensors, and the connection pads, thereby simplifying manufacture of the device. Second, when the sections carrying the thermal sensors are folded together, the thermal sensors are maintained within a thermally and mechanically controlled environment.

Another benefit of the preferred layout shown in FIG. 3 is that the first thermal sensor 120 is physically removed from the heater, in a zone 121 of zero vertical heat flux that is surrounded or encircled by the heater trace 122, and not stacked under it as in the Fox/Solman and Togawa systems. When the temperature measurement device is activated, the heater is turned on and the heat produced thereby travels generally vertically from the heater to the patient, but only medially to the first thermal sensor. As a result, the jump in temperature that occurs when the heater is activated is not immediately sensed by the first thermal sensor, which improves stability of the temperature measurement without requiring an increase in thermal mass of the temperature measurement device. Thus, the first temperature sensor 120 is preferably located in the same plane, or on the same surface, as the heater trace 122 (and can even be elevated slightly above the heater trace), and substantially in or in alignment with the region 121 of zero heat flux.

It is desirable that the temperature measurement device support a pluggable interface for convenience and for modularity of a patient vital signs monitoring system. In this regard, and with reference to FIGS. 3 and 4, the tab 106 is configured with the array of pads 130 so as to be able to slide into and out of connection with a plug. In order to provide a physically robust structure capable of maintaining its shape while being connected and disconnected, the tab 106 is optionally stiffened. In this regard, a flexible stiffener 204 is disposed on the second side 109 of the flexible substrate 100. The stiffener extends substantially coextensively with the tab 106 and partially over the center section 102, at least to the location of the first thermal sensor 120. As best seen in FIG. 4, the stiffener 204 is disposed between the second side 109 of the flexible substrate 100 and the flexible insulator 208. A key to align the tab 106 with an electrical connector (not shown) and to retain the connector on the tab may be provided on the device 200. For example, with reference to FIG. 5, such a key includes an opening 209 through the stiffener and tab. In operation, the opening 209 would receive and retain a retractable, spring-loaded pawl on the casing of a plug.

The temperature measurement device 200 is mounted on a region of skin where temperature is to be measured with the second thermal sensor 126 closest to the skin. As seen in FIG. 4, a layer of adhesive 222 is disposed on the second side 109, on the layer of insulation 140 and the portion of the tail 104 where the second sensor 126 is located. A release liner (not shown in this figure) may be peeled from the layer of adhesive 222 to prepare the device 200 for attachment to the skin. When deployed as shown in FIG. 4, a pluggable signal interface between the electrical circuit on the device 200 and a temperature measurement system is provided through the plurality of electrical connection pads 130 located in the tab 106. The signals transferred therethrough would include at least heater activation and thermal sensor signals.

Use of an electrical circuit on a flexible substrate greatly simplifies the construction of a disposable temperature device for estimating deep tissue temperature, and substantially reduces the time and cost of manufacturing such a device. In this regard, manufacture of a temperature measurement device incorporating an electrical circuit laid out on a side of the flexible substrate 100 with the circuit elements illustrated in FIG. 3 may be understood with reference to FIGS. 5 and 6A-6F. Although a manufacturing method is described in terms of specifically numbered steps, it is possible to vary the sequence of the steps while achieving the same result. For various reasons, some of the steps may include more operations, or fewer, than described. For the same or additional reasons, some of the described steps may be deleted, and/or other steps that are not described may be added. Further, steps may be combined with other steps, and/or partitioned into additional steps.

Figure 6A:
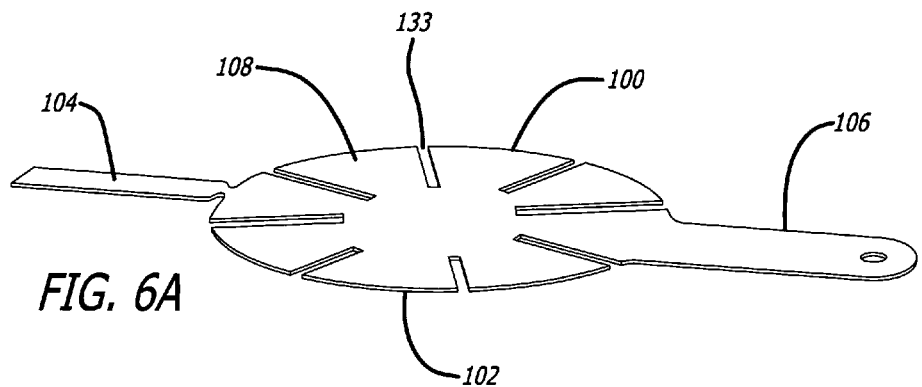
FIGS. 6A-6F illustrate a method of temperature device manufacture based on the temperature device of FIGS. 4 and 5.

In FIG. 6A, the traces and pads for an electrical circuit are fabricated on a first side 108 of a flexible substrate 100 with a center section 102, a tail 104 extending from the center section, and a tab 106 extending from the center section. The electronic elements (first and second thermal sensors) are mounted to the traces to complete an electrical circuit (which is omitted from these figures for convenience) including the elements of FIG. 3, laid out as shown in that figure. If used, the pattern of slits 133 separating the heater zones may be made in the center section in this manufacturing step.

Figure 5:
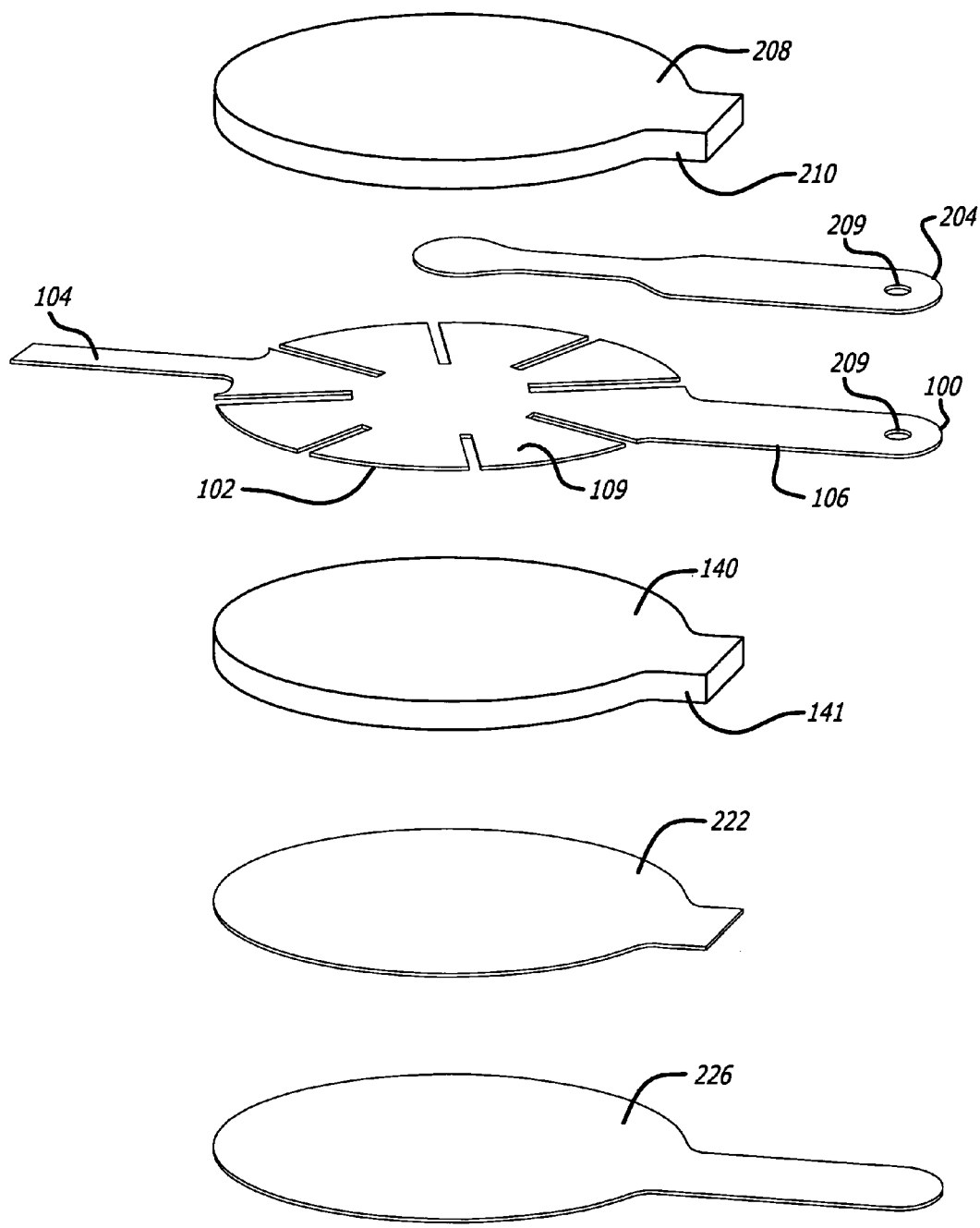
FIG. 5 is an exploded assembly view, in perspective, showing elements of the temperature device of FIG. 4.
Figure 6B:
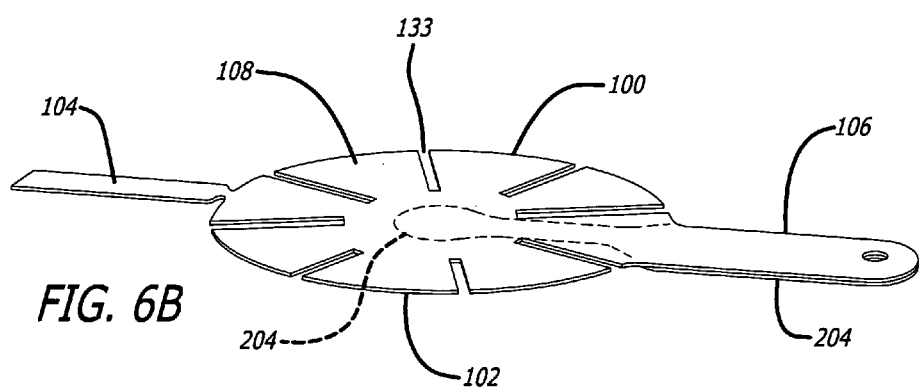
Figure 6C:
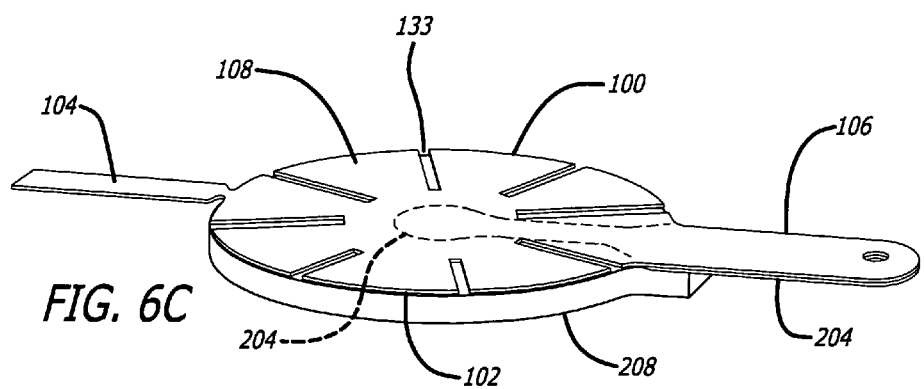

As per FIG. 6B, in a second manufacturing step, a stiffener 204 is laminated to a second side of the flexible substrate. As best seen in FIG. 5, the stiffener has a portion shaped identically to the tab and narrows to an elongated portion with a circular tip. When laminated to the second side 109, the stiffener substantially extends over the tab and partially over the center section, beneath the zone 121 where the first thermal sensor is located. Preferably, an adhesive film (not seen) attaches the stiffener to the second side of the flexible substrate, As per FIG. 6C, in a third manufacturing step, a flexible layer 208 of insulating material is attached by adhesive or equivalent to the first side of the flexible substrate, over substantially all of the center section and at least a portion of the stiffener. This layer is provided to insulate the heater from the ambient environment. As best seen in FIG. 5, this flexible layer may include a truncated tab 210 that provides additional reinforcement to a pluggable connection between the tab 106 and a system plug.

Figure 6D:
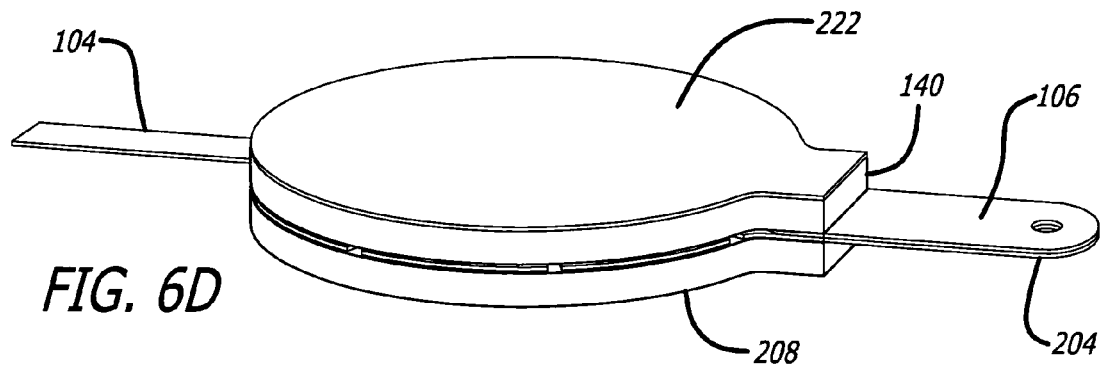

As per FIG. 6D, in a fourth manufacturing step, a flexible central layer of insulating material 140 is attached to the first side 108, over the center section, to cover the heater trace and the first thermal sensor. As best seen in FIG. 5, this flexible layer may also include a truncated tab 141 that provides additional reinforcement to a pluggable connection between the tab and a system plug.

Figure 6E:
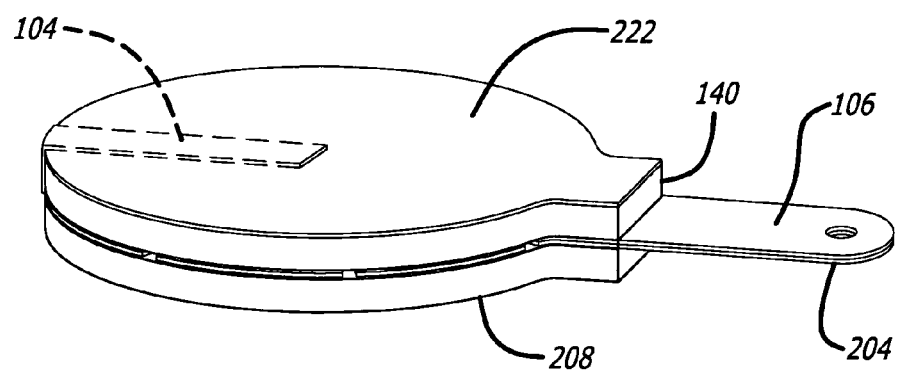

As per FIG. 6E, in a fifth manufacturing step, the tail 104 is folded over the central layer of insulating material 140 such that the first and second thermal sensors are maintained by the central layer in the preferred spaced relationship.

Figure 6F:
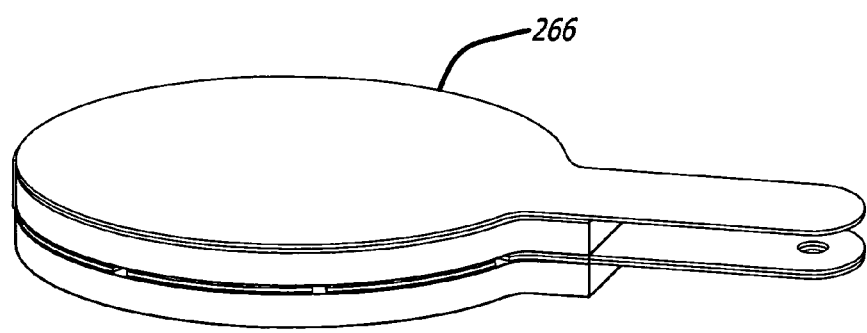

As per FIG. 6F, in a sixth manufacturing step, a layer of adhesive with a release liner 226 is attached to the central insulating layer, over the central insulating layer with the tail folded thereto. As best seen in FIG. 5, the release liner 226 may have a shape that corresponds to the central section 102 and tab 106.

In a best mode of practice, a temperature measurement device according to this specification has been fabricated using the materials and parts listed in the following table. An electrical circuit with copper traces and pads conforming to FIG. 3 was formed on a flexible substrate of polyimide film by a conventional photo-etching technique and thermal sensors were mounted using a conventional surface mount technique. The dimensions in the table are thicknesses, except that Ø signifies diameter. Of course, these materials and dimensions are only illustrative and in no way limit the scope of this specification. For example, traces may be made wholly or partly with electrically conductive ink.

ently preferred embodiments, it should be understood that various modifications can be made without departing from the spirit of the described principles. Accordingly, the principles are limited only by the following claims.

The invention claimed is:

1. A temperature device, comprising:
a flexible substrate; and,
an electrical circuit on a surface of the flexible substrate, the electrical circuit including an annular heater trace surrounding a zone of the surface, a first thermal sensor disposed in the zone, a second thermal sensor disposed outside of the annular heater trace, a plurality of electrical pads disposed outside of the annular heater trace, and a plurality of conductive traces connecting the first and second thermal sensors and the heater trace with the plurality of electrical pads.

2. The temperature device of claim 1, in which sections of the flexible substrate are folded together to place the first and second thermal sensors in proximity to one another, between the sections.

3. The temperature device of claim 2, further including a layer of flexible insulation disposed between the folded-together sections and separating the first and second thermal sensors.

4. A temperature device, comprising:
a flexible substrate;
a first thermal sensor disposed on a first section of the substrate;
a heater trace disposed on the first section with the first thermal sensor;
a second thermal sensor disposed on a second section of the substrate;
a plurality of electrical pads disposed on a third section of the substrate;
a plurality of traces on the flexible substrate connecting the first and second thermal sensors and the heater trace with the plurality of electrical pads;
the first and second sections disposed in a folded-together configuration in which the first and second thermal sensors are positioned in a spaced apart relationship; and,
a flexible insulator disposed between the first and second thermal sensors.

5. The temperature device of claim 4, wherein the first and second thermal sensors and the heater trace are disposed on a first side of the flexible substrate, the temperature device further comprising a flexible insulator disposed on a second side of the flexible substrate, over the first section.

6. The temperature device of claim 5, further comprising a flexible stiffener disposed on the second side of the flexible substrate, substantially coextensively with the third section.

| Table of Materials and Parts | | |
|---|---|---|
| Element | Material | Representative dimensions |
| Flexible substrate | Kapton ® film with deposited and photo-etched copper traces and pads | Substrate 100: 0.05 mm |
| Thermal sensors | NTC thermistors, Part # R603-103F-3435-C, Redfish Sensors | |
| Flexible insulating layers | Closed cell polyethylene foam with skinned major surfaces coated with pressure sensitive adhesive (PSA) | Insulator 208: Ø50 × 1.5 mm<br>Insulator 140: Ø50 × 3.0 mm |
| Stiffener | Polyethylene terephthalate (PET) | Stiffener 204: 0.25 mm |

Although principles of temperature device construction and manufacture have been described with reference to pres- 7. The temperature device of claim 6, further comprising an electrical connector alignment key on the third section.

8. The temperature device of claim 4, further comprising a pattern of slits in the first section.

9. The temperature device of claim 8, wherein the pattern of slits defines a plurality of heater zones occupied by the heater trace.

10. The temperature device of claim 9, wherein the heater zones are wedge shaped.

11. The temperature device of claim 9, wherein each heater zone is flexible independently of any other heater zone.

12. The temperature device of claim 11, further comprising a reduced width of the second section where the first and second sections are joined.

13. The temperature device of claim 4, further comprising a reduced width of the second section where the first and second sections are joined.

14. A temperature device, comprising:
   a flexible substrate having first and second sides;
   the flexible substrate including a circular center section, a tab contiguous with the center section and extending from the center section in a first radial direction, and a tail contiguous with the center section and extending from the center section in a second radial direction;
   a first thermal sensor disposed on the first side, substantially at the center of the center section;
   a heater trace disposed on the first side, in the center section, around the first thermal sensor;
   a second thermal sensor disposed on the first side, in the tail;
   a plurality of electrical pads disposed on the first side, in the tab;
   a plurality of traces disposed on the first side and connecting the first and second thermal sensors and the heater trace with the plurality of electrical pads;
   the center section and the tail folded together to position the first and second thermal sensors in a spaced-apart relationship; and,
   a layer of flexible insulation disposed between the folded-together center section and tail.

15. The temperature device of claim 14, further comprising a flexible stiffening layer attached to the second side and coextensive with the tab and a portion of the center section.

16. The temperature device of claim 15, further comprising a layer of flexible insulation coextensive with the center section and attached to the second side and a portion of the stiffening layer.

17. The temperature device of claim 14, further comprising an electrical connector alignment key on the tab.

18. The temperature device of claim 14, further comprising a pattern of slits in the center section within which the heater trace is disposed.

19. The temperature device of claim 18, wherein the pattern of slits and the heater trace define a multi-zone heater.

20. The temperature device of claim 19, wherein the multi-zone heater includes a plurality of wedge shaped zones.

21. The temperature device of claim 19, wherein each zone is flexible independently of any other zone.

22. The temperature device of claim 14, further comprising a reduced width of the tail where the tail joins the center section.

23. The temperature device of claim 14, further comprising a reduced width of the tail where the center section and tail are folded together.

24. A method of temperature device manufacture, comprising:
   fabricating an electrical circuit on a first side of a flexible substrate with a center section, a tab extending from the center section, and a tail extending from the center section, the electrical circuit including a first thermal sensor disposed on the first side, in the center section, a heater trace disposed on the first side, in the center section, around the first thermal sensor, a second thermal sensor disposed on the first side, in the tail, a plurality of electrical pads disposed on the first side, in the tab, and a plurality of traces disposed on the first side and connecting the first and second thermal sensors and the heater trace with the plurality of electrical pads; and then,
   attaching a flexible heater insulating layer to the second side, over the center section;
   attaching a flexible central insulating layer to the first side, over the center section;
   folding the tail over the central insulating layer; and,
   attaching a layer of adhesive with a release liner to the central insulating layer, over the central insulating layer and the tail.

25. The method of claim 24, further comprising:
   forming the heater trace in a plurality of heater zones; and
   forming a pattern of slits in the center section, each slit separating one heater zone from an adjacent heater zone.

26. The method of claim 25, further comprising, attaching a flexible stiffening layer to the second side, coextensively with the tab and a portion of the center section, followed by attaching the flexible heater insulating layer to the second side, over the center section and a portion of the stiffening layer.

* * * * *

UNITED STATES PATENT AND TRADEMARK OFFICE
CERTIFICATE OF CORRECTION

PATENT NO. : 8,226,294 B2  Page 1 of 1
APPLICATION NO. : 12/584108
DATED : July 24, 2012
INVENTOR(S) : Mark T Bieberich et al.

It is certified that error appears in the above-identified patent and that said Letters Patent is hereby corrected as shown below:

Column 2,
Line 51, after "sensors" insert -- . --.

Column 7,
Lines 11-12, delete "substrate," and insert -- substrate. --, therefor.

Signed and Sealed this
Twenty-third Day of October, 2012

David J. Kappos
*Director of the United States Patent and Trademark Office*